United States Patent
Gattupalli et al.

(10) Patent No.: US 9,950,972 B2
(45) Date of Patent: *Apr. 24, 2018

(54) APPARATUSES AND METHODS FOR FORMING C8 AROMATIC STREAMS WITH SELECTED AMOUNTS OF C9 AROMATICS

(71) Applicant: UOP LLC, Des Plaines, IL (US)

(72) Inventors: Rajeswar Gattupalli, Arlington Heights, IL (US); Jason T. Corradi, Arlington Heights, IL (US); Gregory Werba, Arlington Heights, IL (US); Patrick Whitchurch, Sleepy Hollow, IL (US)

(73) Assignee: UOP LLC, Des Plaines, IL (US)

( * ) Notice: Subject to any disclaimer, the term of this patent is extended or adjusted under 35 U.S.C. 154(b) by 547 days.

This patent is subject to a terminal disclaimer.

(21) Appl. No.: 14/040,341

(22) Filed: Sep. 27, 2013

(65) Prior Publication Data

US 2015/0094512 A1    Apr. 2, 2015

(51) Int. Cl.
*B01D 3/26* (2006.01)
*C07C 7/13* (2006.01)
(Continued)

(52) U.S. Cl.
CPC .............. *C07C 7/005* (2013.01); *B01D 3/143* (2013.01); *B01D 3/26* (2013.01); *C07C 7/04* (2013.01); *C07C 7/13* (2013.01)

(58) Field of Classification Search
None
See application file for complete search history.

(56) References Cited

U.S. PATENT DOCUMENTS 3,558,732 A    1/1971   Neuzil
3,663,638 A    5/1972   Neuzil
(Continued)

FOREIGN PATENT DOCUMENTS

EP    0003622 B1    1/1982
EP    1165471 A1    1/2002
(Continued)

OTHER PUBLICATIONS

Rasouli, et al., "Effect of Nanocrystalline Zeolite Na-Y on Meta-Xylene Separation," Microporous and Mesoporous Materials (2012), 152, 141-147.
(Continued)

*Primary Examiner* — Tam M Nguyen

(57) ABSTRACT

Apparatuses and methods are provided for forming C8 aromatic streams with selected amounts of C9 aromatics. In one embodiment, a method for forming a C8 aromatic stream with a selected amount of C9 aromatics includes fractionating a hydrocarbon stream including C8 and C9 aromatics into a sidedraw fraction and a bottom fraction. The sidedraw fraction includes a portion of the C8 aromatics and a portion of the C9 aromatics. The bottom fraction includes remaining C8 aromatics and C8+ hydrocarbons. The method further includes fractioning the bottom fraction and forming a heavy overhead fraction including the remaining C8 aromatics. Also, the method includes combining the sidedraw fraction and the heavy overhead fraction to form a combined stream having a C9 aromatics composition of from about 0.1 wt % to about 5 wt % about 2 wt % of a total weight of the combined stream.

17 Claims, 2 Drawing Sheets

(51) Int. Cl.
*C07C 7/00* (2006.01)
*B01D 3/14* (2006.01)
*C07C 7/04* (2006.01)

(56) References Cited

U.S. PATENT DOCUMENTS

| | | | |
|---|---|---|---|
| 3,700,744 | A | 10/1972 | Berger et al. |
| 3,813,452 | A | 5/1974 | Bieser |
| 3,855,333 | A | 12/1974 | Neuzil |
| 4,021,499 | A | 5/1977 | Bieser |
| 4,255,607 | A | 3/1981 | Miyake et al. |
| 4,326,092 | A | 4/1982 | Neuzil |
| 4,368,347 | A | 1/1983 | Carra et al. |
| 4,376,226 | A | 3/1983 | Rosenfeld et al. |
| 4,381,419 | A | 4/1983 | Wylie |
| 4,439,535 | A | 3/1984 | Smolin et al. |
| 4,554,398 | A | 11/1985 | Barthomeuf et al. |
| 4,615,994 | A | 10/1986 | Smolin et al. |
| 4,864,069 | A | 9/1989 | Zinnen |
| 4,899,017 | A | 2/1990 | Yan |
| 5,171,922 | A | 12/1992 | Anderson |
| 5,453,560 | A | 9/1995 | Kulprathipanja |
| 5,763,714 | A | 6/1998 | Hickey et al. |
| 5,849,981 | A | 12/1998 | Kulprathipanja |
| 5,884,777 | A | 3/1999 | Pan et al. |
| 5,900,523 | A | 5/1999 | Kulprathipanja |
| 5,912,395 | A | 6/1999 | Noe |
| 6,281,406 | B1 | 8/2001 | Cain |
| 6,706,938 | B2 | 3/2004 | Roeseler et al. |
| 6,841,714 | B2 | 1/2005 | Leflaive et al. |
| 6,896,812 | B1 | 5/2005 | Frey |
| 7,468,468 | B2 | 12/2008 | Leflaive et al. |
| 7,687,674 | B2 | 3/2010 | Wegerer |
| 7,728,187 | B2 | 6/2010 | Kulprathipanja et al. |
| 7,915,471 | B2 | 3/2011 | Leflaive et al. |
| 7,977,526 | B2 | 7/2011 | Porter |
| 8,323,581 | B2 | 12/2012 | Bresler et al. |
| 2006/0287563 | A1* | 12/2006 | Schultz ............. C07C 5/2702 585/481 |
| 2009/0326306 | A1 | 12/2009 | Bresler |
| 2011/0245573 | A1 | 10/2011 | Porter et al. |
| 2012/0004491 | A1 | 1/2012 | Kulprathipanja et al. |
| 2012/0149958 | A1 | 6/2012 | Ellrich |
| 2012/0241384 | A1 | 9/2012 | Porter |
| 2013/0153500 | A1 | 6/2013 | Frey et al. |
| 2013/0153505 | A1 | 6/2013 | Corradi et al. |
| 2013/0158334 | A1 | 6/2013 | Corradi |

FOREIGN PATENT DOCUMENTS

| | | |
|---|---|---|
| WO | 2000058244 | 10/2000 |
| WO | 2006138036 A2 | 12/2006 |
| WO | 2012173755 A2 | 12/2012 |
| WO | 2013089863 A1 | 6/2013 |
| WO | 2013089900 A1 | 6/2013 |
| WO | 2013089901 A1 | 6/2013 |
| WO | 2013089902 A1 | 6/2013 |
| WO | 2013089920 A2 | 6/2013 |
| WO | 2013089921 A1 | 6/2013 |
| WO | 2013089922 A1 | 6/2013 |
| WO | 2013089923 A1 | 6/2013 |

OTHER PUBLICATIONS

Rasouli, et al., "Influence of Monovalent Cations Ion-Exchange on Zeolite ZSM-5 in Separation of Para-Xylene from Xylene Mixture," Microporous and Mesoporous Materials (2012), 150, 47-54.

Bergeot, et al., "Intensification of Paraxylene Production Using a Simulated Moving Bed Reactor," Oil & Gas Science and Technology (2010), 65(5), 721-733.

Guo, et al., "Separation of P-Xylene from C8 Aromatics on Binder-Free Hydrophobic Adsorbent of MFI Zeolite. I. Studies on Static Equilibrium," Microporous and Mesoporous Materials (2000), 39(1-2), 149-161.

Chiang, et al., "Chromatographic Separation of Xylenes with Silicalite," Int. Conf. Fundam. Adsorpt., 3rd (1991), Meeting Date 1989, 199-210, Editor(s): Mersmann, Alfons B.; Scholl, Stephan E.; Publisher: AIChE, New York, N.Y.

EPC Search Report dated Apr. 20, 2017 for corresponding PCT application No. PCT/US2014053067.

* cited by examiner

APPARATUSES AND METHODS FOR FORMING C8 AROMATIC STREAMS WITH SELECTED AMOUNTS OF C9 AROMATICS

TECHNICAL FIELD

The present disclosure generally relates to apparatuses and methods for processing hydrocarbons during the production of desired isomers of xylene, and more particularly relates to apparatuses and methods for forming C8 aromatic streams with selected amounts of C9 aromatics.

BACKGROUND

Aromatic hydrocarbons can be processed to form product streams of a selected isomer of xylene. Xylene is an aromatic hydrocarbon that includes a benzene ring and two methyl substituents. Based on the structural position of the methyl substituents, three isomers of xylene can be formed: paraxylene, metaxylene, and orthoxylene. Paraxylene is a feedstock for terephthalic acid, which is used in the manufacture of synthetic fibers and resins. Metaxylene is used in the manufacture of certain plasticizers, azo dyes, and wood preservatives. Orthoxylene is a feedstock for phthalic anhydride, which is used in the manufacture of certain plasticizers, dyes, and pharmaceutical products.

For production of a desired xylene isomer, a mixed stream of the three xylene isomers is typically produced before the desired xylene isomer is separated. In other words, the desired xylene is not selectively produced but is selectively separated. A desired xylene isomer can be separated from mixed xylene streams by using an adsorbent selective to the desired isomer. After the desired isomer is adsorbed from the mixed xylene stream, the remaining isomers are discharged in a mixed raffinate stream. Typically, a desorbent desorbs the desired xylene isomer from the adsorbent, and the desorbent and selected xylene isomer are collected and separated by fractionation.

In the production of paraxylene, heavy desorbents are conventionally used to desorb the paraxylene from the adsorbent. Heavy desorbents are defined as having higher molecular weights and higher boiling points than xylene. Accordingly, light desorbents are defined as having lower molecular weights and lower boiling points than xylene. Heretofore, xylene isomer recovery systems using heavy desorbents have typically required less energy than systems with light desorbents, because the heavy desorbent does not require repeated evaporation and lifting during fractionation. However, heavy desorbent systems typically require stringent feed purity to control accumulation of undesired compounds in the recycled desorbent, such as impurities that reduce desorbent effectiveness and product purity. Further, additional equipment may be required to maintain heavy desorbent purity during the desorbent recycling process. Also, systems using heavy desorbent have fractionation columns with relatively higher reboiler temperatures. Higher reboiler temperatures lead to higher operating pressures that require higher pressure ratings for the equipment involved, thereby increasing the equipment capital cost.

Use of a light desorbent, such as the relatively inexpensive light desorbent toluene, relaxes feed specifications relative to systems using heavy desorbent. Cost savings for the relaxed feed specifications can offset the increased energy costs associated with recovering light desorbent as a fractionation column overhead. Xylene recovery apparatuses using light desorbent also provide savings in the total equipment count as desorbent purification and storage units are not necessary. Further, xylene recovery apparatuses using light desorbent have lower fractionation column operating pressures, allowing for less expensive thinner column shells with lower pressure ratings.

To efficiently produce a selected xylene isomer product from a hydrocarbon stream using light desorbent, it is generally desirable to separate substantially all of the aromatic hydrocarbons having eight carbon atoms (C8), including xylene and ethylbenzene, from the hydrocarbon stream and from recycled portions of the stream during processing to form a mixed xylene stream for separation into a selected xylene isomer stream. Conventional processes have attempted to eliminate aromatic C9 from the mixed xylene stream. This is particularly true of conventional heavy desorbent systems because the heavy desorbent becomes polluted by aromatic C9 during xylene isomer separation. Further, the energy needed to affect proper separation of xylene isomers is reduced when the aromatic C8 in the mixed xylene stream fed to the separation unit is made less pure. Despite this energy savings a relatively pure aromatic C8 feed stream for the separation unit is still desirable for the production of selected xylene isomer products.

Accordingly, it is desirable to provide methods and apparatuses for forming C8 aromatic streams with selected amounts of C9 aromatics. In addition, it is desirable to develop methods and apparatuses for efficiently producing selected xylene isomer products from hydrocarbon streams. Furthermore, other desirable features and characteristics of the present embodiment will become apparent from the subsequent detailed description and the appended claims, taken in conjunction with the accompanying drawings and this background.

BRIEF SUMMARY

Apparatuses and methods are provided for forming C8 aromatic streams with selected amounts of C9 aromatics. In an exemplary embodiment, a method for forming a C8 aromatic stream with a selected amount of C9 aromatics includes fractionating a hydrocarbon stream including C8 and C9 aromatics into a sidedraw fraction and a bottom fraction. The sidedraw fraction includes a portion of the C8 aromatics and a portion of the C9 aromatics. The bottom fraction includes remaining C8 aromatics and C8$^+$ hydrocarbons. The method further includes fractioning the bottom fraction and forming a heavy overhead fraction including the remaining C8 aromatics. Also, the method includes combining the sidedraw fraction and the heavy overhead fraction to form a combined stream having a C9 aromatics composition of from about 0.1 wt % to about 5 wt % of a total weight of the combined stream.

In another embodiment, a method for forming a selected xylene isomer product is provided. The method for forming a selected xylene isomer product includes feeding a hydrocarbon stream including C8 aromatics and C9 aromatics to a fractionation unit. The method forms a sidedraw fraction from the hydrocarbon stream. The sidedraw fraction includes C8 aromatics and at least 1 wt % C9 aromatics. The method forms a bottom fraction from the hydrocarbon stream. The bottom fraction includes C8$^+$ hydrocarbons and at least 5% of the C8 aromatics from the hydrocarbon stream. The method further includes feeding the bottom fraction to a heavy aromatics fractionation unit and forming a heavy overhead fraction from the bottom fraction. The heavy overhead fraction includes substantially all of the C8 aromatics in the bottom fraction. The method further separates a selected xylene isomer from the sidedraw fraction and from the heavy overhead fraction to form the selected xylene isomer product.

Another embodiment provides an apparatus for forming a C8 aromatic stream with a selected amount of C9 aromatics. The apparatus includes a first fractionation unit configured to receive a hydrocarbon stream and to form an overhead fraction including C7− hydrocarbons, a sidedraw fraction including about 80% to about 95% of the C8 aromatics from the hydrocarbon stream, and a bottom fraction including about 5% to about 20% of the C8 aromatics from the hydrocarbon stream. The sidedraw fraction is formed with a C9 aromatics composition of about 1 wt % to about 2 wt % of a total weight of the sidedraw fraction. The apparatus further includes a second fractionation unit configured to receive the bottom fraction and to form a heavy overhead fraction including substantially all of the C8 aromatics from the bottom fraction.

BRIEF DESCRIPTION OF THE DRAWINGS

The present embodiment will hereinafter be described in conjunction with the following drawing figures, wherein like numerals denote like elements, and wherein.

DETAILED DESCRIPTION

The following detailed description is merely exemplary in nature and is not intended to limit the application and uses of the embodiment described. Furthermore, there is no intention to be bound by any theory presented in the preceding background or the following detailed description.

The various embodiments described herein relate to apparatuses and methods for forming C8 aromatic streams with selected non-zero amounts of C9 aromatics. Such streams may be used as the mixed xylenes feed to a xylene isomer separation process utilizing a light desorbent such as toluene. It has been found that while the efficiency of xylene isomer recovery in a xylene isomer separation process is decreased by the inclusion of non-zero amounts of C9 aromatics in the mixed xylenes feed, the cost increase of such inefficiency is more than offset by the cost savings in the formation of the mixed xylene stream. Specifically, as described below, a hydrocarbon stream is fractionated to produce a sidedraw fraction of a mixed xylene stream with aromatic hydrocarbons containing 8 carbon atoms (aromatic C8) and with aromatic hydrocarbons containing 9 carbon atoms (aromatic C9). Further, the fractionation process forms a bottom fraction containing a remaining portion of the aromatic C8. The bottom fraction is fractionated to form a heavy overhead fraction containing the remaining aromatic C8. In this manner, the aromatic C8 is efficiently isolated from the hydrocarbon stream. Further, the combined stream formed from the sidedraw fraction and the heavy overhead fraction has a sufficient aromatic C8 composition and a sufficiently low aromatic C9 composition to allow for efficient separation of a selected xylene isomer in further downstream processing. As used herein, the phrase "overhead fraction" and term "overhead" are not limited to the uppermost fraction from a fractionation process or apparatus, but may include the uppermost fraction and/or any fraction formed above the sidedraw and bottom fraction. Further, as used herein, the phrase "bottom fraction" and term "bottom" is not limited to the lowermost fraction from a fractionation process or apparatus, but may include the lowermost fraction and/or any fraction formed below the sidedraw and overhead fraction.

Figure 1:
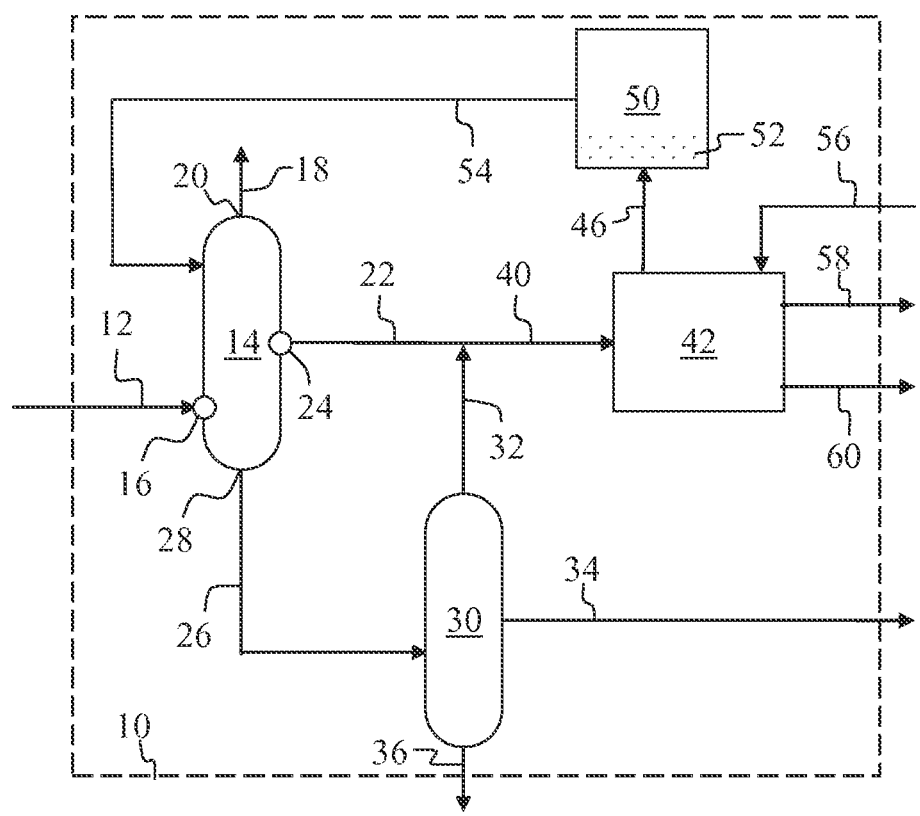
FIG. 1 is a schematic diagram of an exemplary embodiment of a method and an apparatus for forming C8 aromatic streams with selected amounts of C9 aromatics.

Reference is now made to an exemplary embodiment of an apparatus 10 for forming a C8 aromatic stream with selected amounts of C9 aromatics in FIG. 1. A hydrocarbon stream 12 is fed to a fractionation unit 14, such as a stripper column, at a feed point 16. An exemplary hydrocarbon stream 12 has a relatively high concentration of aromatic compounds, such as about 40 to about 100 mass percent. Suitable hydrocarbon streams 12 are available from many sources. For example, a fluid catalytic cracking (FCC) unit and fractionator run in high severity mode can produce a fraction with hydrocarbons having 7 to 10 carbon atoms (C7-10), where about 60 mass percent of the hydrocarbons are aromatic. Certain coal liquefaction processes produce hydrocarbon streams rich in aromatic compounds, and these hydrocarbon streams are suitable for use as hydrocarbon stream 12. Other possible sources include various petroleum refining processes, thermal or catalytic cracking of hydrocarbons, or petrochemical conversion processes, including hydrocarbon streams processed in a reformer using a catalyst designed to produce aromatic compounds. Additional processing steps (not illustrated in FIG. 1) can be used to remove non-aromatic compounds from the hydrocarbon stream 12 in some embodiments, such as liquid liquid extraction, extractive crystallization, clay treating, or additional fractionation.

The fractionation unit 14 is operated at conditions suitable for forming an overhead fraction 18 primarily containing hydrocarbons having seven and fewer carbon atoms (C7−) that exits the fractionation unit 14 at or around its top 20. An exemplary overhead fraction 18 contains more than about 80%, for example more than about 90%, such as more than about 95%, hydrocarbons having seven and fewer carbon atoms. The fractionation unit 14 further forms a sidedraw fraction 22 primarily containing aromatic hydrocarbons having eight carbon atoms (C8) that exits the fractionation unit 14 at a draw point 24. An exemplary sidedraw fraction 22 is rich in aromatic C8 and contains more than about 80%, for example more than about 90%, such as more than about 95%, or more than about 98%, aromatic hydrocarbons having eight carbon atoms.

The sidedraw fraction 22 may be considered to form a mixed xylene stream. In an exemplary embodiment, the sidedraw fraction includes about 80% to about 95% of the C8 aromatics from the hydrocarbon stream. In another embodiment, the sidedraw fraction includes no more than about 92% of the C8 aromatics in the hydrocarbon stream, such as about 90% of the C8 aromatics in the hydrocarbon stream. An exemplary sidedraw fraction 22 has a C9 aromatics composition of less than about 2 wt %. An exemplary sidedraw fraction 22 includes at least 1 wt % C9 aromatics. In certain embodiments, the sidedraw fraction has a C9 aromatics composition of about 1 wt % to about 2 wt %.

The fractionation unit 14 also forms a bottom fraction 26 primarily containing hydrocarbons having eight and more carbon atoms (C8+) that exits from the fractionation unit 14 at or around its bottom 28. An exemplary bottom fraction 26 contains more than about 80%, for example more than about 90%, such as more than about 95%, hydrocarbons having eight and more carbon atoms. In an exemplary embodiment, the bottom fraction includes at least 5% of the C8 aromatics from the hydrocarbon stream, such as about 5% to about 20% of the C8 aromatics from the hydrocarbon stream, for example about 10% of the C8 aromatics in the hydrocarbon stream.

The different fractions (such as C7$^-$, C8, and C8$^+$) are separated based on the relative boiling points of the compounds present. To provide desired separation, the fractionation unit 14 can be operated from a pressure of about 5 kiloPascals absolute (kPa) to about 1,800 kPa (about 0.7 pounds per square inch absolute (PSIA) to about 260 PSIA), and a temperature from about 35° C. to about 360° C. (about 65° F. to about 680° F.).

As shown, the draw point 24 is located above the feed point 16, i.e., between the feed point 16 and the top 20 of the fractionation unit 14. Likewise, the feed point 16 is located below the draw point 24, i.e., between the draw point 24 and the bottom 28 of the fractionation unit 14. In an exemplary embodiment, the fractionation unit 14 is formed with trays and the draw point 24 is located at a higher tray than the feed point 16. By providing the draw point 24 above the feed point 16, recovery of relatively heavier species, such as hydrocarbons having nine or more carbon atoms (C9$^+$) in the sidedraw fraction 22 is inhibited.

In FIG. 1, the bottom fraction 26, containing C8$^+$ species including some aromatic C8, is introduced to a heavy aromatics fractionation unit 30. The heavy aromatics fractionation unit 30 is operated at conditions suitable for forming a heavy overhead fraction 32 that contains substantially all of the aromatic C8 that is introduced into the heavy aromatics fractionation unit 30 in the bottom fraction 26. The heavy overhead fraction 32 may be considered to form a mixed xylene stream. In an exemplary embodiment, the heavy overhead fraction has a C9 aromatics composition of less than about 2.0 wt %. The heavy aromatics fractionation unit 30 also forms a heavy sidedraw fraction 34 that contains aromatic hydrocarbons having nine or ten carbon atoms (C9-C10) and a heavy bottom fraction 36 that contains hydrocarbons having eleven and more carbon atoms (C11$^+$). The heavy sidedraw fraction 34 and the heavy bottom fraction 36 may exit the apparatus 10 for further processing.

The different fractions (such as C8, C9-C10, and C11$^+$) are separated in the heavy aromatics fractionation unit 30 based on the relative boiling points of the compounds present. The heavy aromatics fractionation unit 30 can be operated from a pressure of about 5 kPa to about 1800 kPa (about 0.7 PSIA to about 260 PSIA), and a temperature from about 100° C. to about 360° C. (about 212° F. to about 680° F.).

The mixed xylene streams, i.e., the sidedraw fraction 22 from the fractionation unit 14 and the heavy overhead fraction 32 from the heavy aromatics fractionation unit 30, are combined to form a combined mixed xylene stream 40. An exemplary combined mixed xylene stream 40 has a C9 aromatics composition of from about 0.5 wt % to about 5 wt %, such as from about 1 wt % to about 2 wt %, for example about 1.6 wt %. Further, the exemplary combined mixed xylene stream 40 includes substantially all of the aromatic C8 from the hydrocarbon stream 12.

In an exemplary embodiment, the combined mixed xylene stream 40 is further processed to isolate a selected xylene isomer. Therefore, the combined mixed xylene stream 40 is introduced into a separation unit 42 that separates a selected xylene isomer from non-selected xylene isomers. An exemplary separation unit 42 includes a selective adsorbent that preferentially sorbs the selected xylene isomer relative to the other xylene isomers. A desorbent is then used to desorb the selected xylene isomer from the adsorbent, and the desorbent and selected xylene isomer are collected and separated by distillation. In an exemplary embodiment, the selective adsorbent is crystalline alumino-silicate, such as type X or type Y crystalline aluminosilicate zeolites. The exemplary selective adsorbent contains exchangeable cationic sites with one or more metal cations, where the metal cations can be one or more of lithium, potassium, beryllium, magnesium, calcium, strontium, barium, nickel, copper, silver, manganese, and cadmium. Sorption conditions vary, but typically range from about 35° C. to about 200° C. (about 100° F. to about 400° F.) and from about 100 kPa to about 3,500 kPa (about 14 PSIA to about 500 PSIA).

Separation of the selected xylene isomer from the non-selected xylene isomers results in the formation of a raffinate xylene isomer stream 46 containing the non-selected xylene isomers. In the exemplary apparatus 10, the raffinate xylene isomer stream 46 is fed to an isomerization unit 50 where the non-selected xylene isomers are isomerized to produce more of the selected xylene isomer. Specifically, the removal of the selected xylene isomer in the separation unit 42 shifts the composition of the raffinate xylene isomer stream 46 away from the equilibrium between isomer species. Because the raffinate xylene isomer stream 46 primarily includes the non-selected two of the three xylene isomers and is relatively deficient in the selected xylene isomer, the selected xylene isomer is produced in the isomerization unit 50 to bring the xylene isomers closer to an equilibrium ratio. At about 250° C., the equilibrium ratio is about 20 to 25 percent orthoxylene, 20 to 30 percent paraxylene, and 50 to 60 percent metaxylene, though the equilibrium ratio varies with temperature and other conditions.

In an exemplary embodiment, the isomerization unit 50 includes an isomerization catalyst 52, and operates at suitable isomerization conditions. Suitable isomerization conditions include a temperature from about 100° C. to about 500° C. (about 200° F. to about 900° F.), or from about 200° C. to about 400° C. (about 400° F. to about 800° F.), and a pressure from about 500 kPa to about 5,000 kPa (about 70 PSIA to about 700 PSIA). The isomerization unit 50 includes a sufficient volume of isomerization catalyst to provide a liquid hourly space velocity, with respect to the raffinate xylene isomer stream 46, from about 0.5 to about 50 hr$^{-1}$, or from about 0.5 to about 20 hr$^{-1}$. Hydrogen may be present at up to about 15 moles of hydrogen per mole of xylene, but in some embodiments hydrogen is essentially absent from the isomerization unit 50. The isomerization unit 50 may include one, two, or more reactors, where suitable means are employed to ensure a suitable isomerization temperature at the entrance to each reactor. The xylenes are contacted with the isomerization catalyst in any suitable manner, including upward flow, downward flow, or radial flow.

An exemplary isomerization catalyst includes a zeolitic aluminosilicate with a Si:Al$_2$ ratio greater than about 10/1, or greater than about 20/1 in some embodiments, and a pore diameter of about 5 to about 8 angstroms. Some examples of suitable zeolites include, but are not limited to, MFI, MEL, EUO, FER, MFS, MTT, MTW, TON, MOR, and FAU, and gallium may be present as a component of the crystal structure. In some embodiments, the Si:Ga$_2$ mole ratio is less than 500/1, or less than 100/1 in other embodiments. The proportion of zeolite in the catalyst is generally from about 1 weight percent (wt %) to about 99 wt %, or from about 25 wt % to about 75 wt %. In some embodiments, the isomerization catalyst includes about 0.01 wt % to about 2 wt % of one or more of ruthenium (Ru), rhodium (Rh), palladium (Pd), osmium (Os), Iridium (Ir), and platinum (Pt), but in other embodiments the isomerization catalyst is substantially absent of any metallic compound, where substantial absence is less than about 0.01 wt %. The balance of the isomerization catalyst is an inorganic oxide binder, such as alumina, and a wide variety of catalyst shapes can be used, including spherical or cylindrical.

An isomerized stream 54 with an equilibrium distribution of xylene isomers exits the isomerization unit 50 and is recycled to the fractionation unit 14. The xylenes in the isomerized stream 54 continue on to the separation unit 42 via the sidedraw fraction 22 or the heavy overhead fraction 32. In the exemplary apparatus 10, the isomerized stream 54 is passed through the fractionation unit 14 so that C8 compounds that were changed to a compound with a different number of carbon atoms in the isomerization unit 50 can be removed via fractions 18, 34 or 36. The isomerized stream 54 includes more of the selected xylene isomers than the raffinate xylene isomer stream 46, so more of the selected xylene isomer is available for recovery in the separation unit 42. As a result, the amount of the recovered selected xylene isomer can exceed its theoretical equilibrium value at processing temperatures.

Separation of the selected xylene isomer from the non-selected xylene isomers in the separation unit 42 further results in the formation of an extract stream (not illustrated) containing the selected xylene isomer and the desorbent. Within the separation unit 42, the desorbent 56 is used to desorb the selected xylene isomer from the adsorbent. The desorbent 56 and the selected xylene isomer will form the extract stream, which is fed to an extract column (not shown). The desorbent 56 is then separated from the selected xylene isomer by fractionation in an extract column (not shown) in the separation unit 42. The selected xylene isomer exits the extract column as a bottoms stream that, if required, can be sent to a finishing column to further purify the selected xylene stream to meet product quality specification. The selected xylene stream leaves the finishing column as an overhead fraction and is discharged from the separation unit 42 as product stream 58. Product stream 58 can be removed from the apparatus 10 as the selected xylene product, e.g., a paraxylene product, an orthoxylene product, or a metaxylene product. The bottoms stream from the finishing column may include some selected xylene isomer and is discharged from the separation unit 42 as stream 60.

Several different embodiments of the separation unit 42 are possible, such as a single bed operated in batch fashion, where the raffinate xylene isomer stream 46 is collected before the selected xylene isomer is desorbed, and the extract stream is collected after desorbing. In another embodiment, multiple adsorbent beds are used, and the introduction point of the combined mixed xylene stream 40 and the desorbent 56 are gradually moved through the different adsorbent beds. The discharge points of the extract stream and the raffinate xylene isomer stream 46 are also gradually moved through the different adsorbent beds, so each individual adsorbent bed is used in a semi-batch mode and the combination simulates a continuous operation. As a light desorbent, desorbent 56 has a lower molecular weight than xylene as well as a desorbent boiling point lower than the selected xylene isomer boiling point or the non-selected xylene isomer(s) boiling point.

Figure 2:
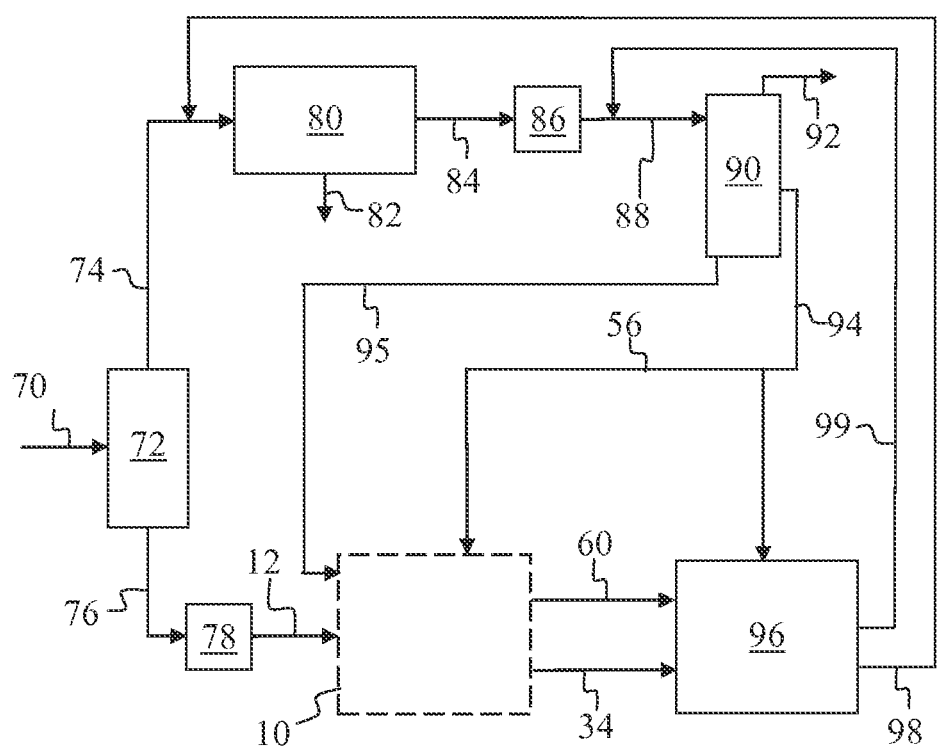
FIG. 2 is a schematic diagram of the method and the apparatus of FIG. 1 in use in a scheme for producing a selected xylene isomer product.

Referring to FIG. 2, the apparatus 10 is shown in integration with other hydrocarbon processing scheme. As shown, the hydrocarbon stream 12 is formed from a feed stream 70. An exemplary feed stream 70 is a naphtha feedstock. Naphtha feedstocks include aromatics, paraffins, and naphthenes, and may include small amounts of olefins. Feedstocks which may be utilized include straight-run naphthas, natural gasoline, synthetic naphthas, thermal gasoline, catalytically cracked gasoline, and in particular reformed naphthas. The feedstock may be encompassed by a full-range naphtha as defined by boiling points, or from about 0° to about 230° C., or naphthas having a greater percentage, such as greater than about 50% or greater than about 70%, of aromatic hydrocarbons.

As shown in FIG. 2, the feed stream 70, particularly in embodiments where the feed stream 70 is a reformed naphtha stream, is fed to a reformate splitter distillation column 72. The reformate splitter distillation column 72 functions to separate or "split" by distilling the feed stream 70 into a lower boiling stream as an overhead stream 74 and a higher boiling stream as a bottom stream 76. The reformate splitter distillation column may be configured such that, for example, the overhead stream 74 may include primarily (such as greater than about 80%, greater than about 90%, or greater than about 95%) hydrocarbons having seven or fewer carbon atoms ($C7^-$). The bottom stream 76 may thus include primarily, such as greater than about 80%, greater than about 90%, or greater than about 95%, hydrocarbons having eight or more carbon atoms ($C8^+$).

The bottom stream 76 may thereafter be passed to a clay treater 78 for the removal of any alkylates and olefins that may be present in the bottom stream 76. The clay treater 78 may be configured in any known manner suitable for this purpose. The hydrocarbon stream 12 leaving the clay treater 78 may thus include primarily, such as greater than about 80%, greater than about 90%, or greater than about 95%, $C8^+$ hydrocarbons with alkylate and olefin compounds substantially, such as greater than about 90%, removed therefrom.

The overhead stream 74 is passed from the reformate splitter distillation column 72 to an extractive distillation process unit 80 for removing non-aromatic compounds from the overhead stream 74. In one particular embodiment, extractive distillation process unit 80 may employ a sulfolane solvent to separate aromatic compounds from non-aromatic compounds. Other extraction methods, such as liquid-liquid solvent extraction are also well-known and practiced for separation of non-aromatic compounds from aromatic compounds, and their use in place of, or in addition to, extractive distillation process unit 80 is contemplated herein. Extractive distillation process unit 80 produces a stream 82 that includes primarily, such as greater than about 80%, greater than about 90%, or greater than about 95%, non-aromatic $C7^-$ hydrocarbons and a stream 84 that includes primarily, such as greater than about 80%, greater than about 90%, or greater than about 95%, benzene and toluene. Stream 84 may further be passed to a clay treater 86 for increasing the purity of the aromatic compounds in such stream, for example by removing any alkylates or olefins that may be present therein in a manner as described above with regard to clay treater 78, thus producing a treated benzene and toluene stream 88.

The treated benzene and toluene stream 88 is thereafter passed to a split shell distillation column 90 for the separation of the benzene from the toluene in the treated benzene and toluene stream 88. The benzene, having a lower boiling point than toluene, is removed from distillation column 90 as an overhead product 92, and the toluene, having a higher boiling point than benzene, is removed from distillation column 90 as a sidedraw product 94. Also, a net bottoms liquid stream 95 including heavier aromatic hydrocarbons such as various xylene isomers, is removed from the distillation column 90 and thereafter fed to the apparatus 10, and more specifically to the fractionation unit 14 of FIG. 1.

The toluene in the sidedraw product 94 may be fed to the apparatus 10, and more specifically to the adsorbent chamber in the separation unit 42 as desorbent 56. Alternatively or additionally, the sidedraw product 94 is fed to a transalkylation unit process unit 96. As shown, the transalkylation process unit 96 also receives the heavy sidedraw fraction 34 that contains aromatic hydrocarbons having nine or ten carbon atoms (C9-C10) and exits the heavy aromatics fractionation unit 30 (see FIG. 1) in the apparatus 10. Also, the transalkylation process unit 96 receives the stream 60 that may include some selected xylene isomer and that exits the finishing column in the separation unit 42 (see FIG. 1) of apparatus 10.

The transalkylation process unit 96 converts the toluene into benzene and xylenes in a toluene disproportionation process. Further, the transalkylation process unit 96 converts a mixture of toluene and aromatic hydrocarbons having nine carbon atoms (C9) into xylenes in a transalkylation process. Hydrogen is fed to the transalkylation process unit 96 so that the disproportionation and transalkylation processes are conducted in a hydrogen atmosphere to minimize coke formation. As shown, a stream 98 including benzene and toluene exits the Transalkylation process unit 62 and may thereafter be passed to the extractive distillation process unit 80 for removing any non-aromatic compounds therein formed during the disproportionation and transalkylation processes. Also, a stream 99 of toluene and xylenes exits the transalkylation process unit 62 and is fed to the split shell distillation column 90 for the separation of toluene from the xylenes.

As described herein, an apparatus and method for forming a C8 aromatic stream with selected amounts of C9 aromatics are provided. The apparatus uses two fractionation units to form an aromatic C8-rich sidedraw fraction including a selected amount of C9 aromatics and to form a heavy overhead fraction including the remaining aromatic C8. By operating the fractionation unit to form the sidedraw fraction with aromatic C8 and a selected amount of aromatic C9, a substantial energy savings is made. This cost savings compensates for the relatively higher cost of recovering a selected xylene isomer from the mixed xylene stream containing aromatic C9.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the application in any way. Rather, the foregoing detailed description will provide those skilled in the art with a convenient road map for implementing one or more embodiments, it being understood that various changes may be made in the function and arrangement of elements described in an exemplary embodiment without departing from the scope, as set forth in the appended claims.

The invention claimed is:

1. A method for forming a C8 aromatic stream with a selected amount of C9 aromatics, the method comprising the steps of:
   fractionating a hydrocarbon stream including C8 aromatics and C9 aromatics into a sidedraw fraction including a portion of the C8 aromatics and a portion of the C9 aromatics, and a bottom fraction including remaining C8 aromatics and $C8^+$ hydrocarbons;
   fractionating the bottom fraction and forming a heavy overhead fraction including the remaining C8 aromatics; and
   combining the sidedraw fraction and the heavy overhead fraction to form a combined stream having a C9 aromatics composition of 0.5 wt % to 5 wt %; and
   feeding the combined stream containing C8 aromatics and C9 aromatics to a separation unit;
   contacting the combined stream with an adsorbent in the separation unit and adsorbing a selected xylene isomer from the combined stream to form an extract stream and a raffinate stream, wherein the extract stream comprises adsorbed xylene isomer and a portion of C9 aromatics and the raffinate stream comprises non-selected xylene isomers and the remaining portion of C9 aromatics;
   contacting the adsorbed xylene isomer with a desorbent and desorbing the selected xylene isomer from the adsorbent to form a stream of desorbent and the selected xylene isomer; and
   separating the desorbent and the selected xylene isomer.

2. The method of claim 1 wherein combining the sidedraw fraction and the heavy overhead fraction forms a combined stream having a C9 aromatics composition of from about 1 wt % to about 2 wt % of a total weight of the combined stream.

3. The method of claim 1 wherein combining the sidedraw fraction and the heavy overhead fraction forms a combined stream having a C9 aromatics composition of about 1.6 wt % of a total weight of the combined stream.

4. The method of claim 1 wherein fractionating the hydrocarbon stream comprises forming the sidedraw fraction with a C9 aromatics composition of less than about 2 wt % of a total weight of the sidedraw fraction.

5. The method of claim 1 wherein fractionating the bottom fraction and forming a heavy overhead fraction including the remaining C8 aromatics comprises forming the heavy overhead fraction with a C9 aromatics composition of less than about 2.0 wt % of a total weight of the heavy overhead fraction.

6. The method of claim 1 wherein fractionating the hydrocarbon stream comprises forming the sidedraw fraction with about 90% of the C8 aromatics in the hydrocarbon stream and forming the bottom fraction with about 10% of the C8 aromatics in the hydrocarbon stream.

7. The method of claim 1 wherein fractionating the hydrocarbon stream comprises forming the sidedraw fraction with no more than about 92% of the C8 aromatics in the hydrocarbon stream.

8. The method of claim 1 further comprising separating a selected xylene isomer from the combined stream.

9. A method for forming a selected xylene isomer product, the method comprising the steps of:
   feeding a hydrocarbon stream including C8 aromatics and C9 aromatics to a fractionation unit;
   forming a sidedraw fraction from the hydrocarbon stream, wherein the sidedraw fraction includes C8 aromatics and at least 1 wt % C9 aromatics of a total weight of the sidedraw fraction;
   forming a bottom fraction from the hydrocarbon stream, wherein the bottom fraction includes $C8^+$ hydrocarbons and at least 5% of the C8 aromatics from the hydrocarbon stream;
   feeding the bottom fraction to a heavy aromatics fractionation unit;
   forming a heavy overhead fraction from the bottom fraction, wherein the heavy overhead fraction includes substantially all of the C8 aromatics in the bottom fraction;

separating a selected xylene isomer from the sidedraw fraction and from the heavy overhead fraction to form the selected xylene isomer product.

10. The method of claim 9 further comprising combining the sidedraw fraction and the heavy overhead fraction to form a combined stream having a C9 aromatics composition of from about 0.5 wt % to about 5 wt % of a total weight of the combined stream.

11. The method of claim 9 further comprising combining the sidedraw fraction and the heavy overhead fraction to form a combined stream having a C9 aromatics composition of from about 1 wt % to about 2 wt % of a total weight of the combined stream.

12. The method of claim 9 further comprising combining the sidedraw fraction and the heavy overhead fraction to form a combined stream having a C9 aromatics composition of about 1.6 wt % of a total weight of the combined stream.

13. The method of claim 9 wherein forming a sidedraw fraction from the hydrocarbon stream comprises forming the sidedraw fraction with a C9 aromatics composition of less than about 2 wt % of a total weight of the sidedraw fraction.

14. The method of claim 9 wherein forming a heavy overhead fraction from the bottom fraction comprises forming the heavy overhead fraction with a C9 aromatics composition of less than about 2.0 wt % of a total weight of the heavy overhead fraction.

15. The method of claim 9 wherein forming a sidedraw fraction from the hydrocarbon stream comprises forming the sidedraw fraction with about 90% of the C8 aromatics in the hydrocarbon stream, and wherein forming a heavy overhead fraction from the bottom fraction comprises forming the heavy overhead fraction with about 10% of the C8 aromatics in the hydrocarbon stream.

16. The method of claim 9 wherein forming a sidedraw fraction from the hydrocarbon stream comprises forming a sidedraw fraction with no more than about 92% of the C8 aromatics in the hydrocarbon stream.

17. The method of claim 9 wherein separating a selected xylene isomer from the sidedraw fraction and from the heavy overhead fraction to form the selected xylene isomer product comprises:
   combining the sidedraw fraction and the heavy overhead fraction to form a combined mixed xylenes stream;
   feeding the combined mixed xylenes stream containing C8 aromatics and C9 aromatics to a separation unit;
   contacting the combined mixed xylenes stream with an adsorbent in the separation unit and adsorbing a selected xylene isomer from the combined mixed xylenes stream to form an extract stream and a raffinate stream, wherein the extract stream comprises adsorbed xylene isomer and a portion of C9 aromatics and the raffinate stream comprises non-selected xylene isomers and the remaining portion of C9 aromatics;
   contacting the adsorbed xylene isomer with a desorbent and desorbing the selected xylene isomer from the adsorbent to form a stream of desorbent and the selected xylene isomer; and
   separating the desorbent and the selected xylene isomer to form the selected xylene isomer product.

* * * * *